United States Patent [19]

Maronian et al.

[11] Patent Number: 5,059,486
[45] Date of Patent: Oct. 22, 1991

[54] SELF-HEALING RUBBER ARTICLE AND METHOD

[75] Inventors: Hovaness H. Maronian, Rochester; Malur R. Balaji, Pittsford, both of N.Y.

[73] Assignee: Rochester Medical Devices, Inc., Rochester, N.Y.

[21] Appl. No.: 370,817

[22] Filed: Jun. 23, 1989

[51] Int. Cl.$^5$ .................. B32B 25/08; B32B 27/08; B29C 55/00
[52] U.S. Cl. .................. 428/493; 264/288.4; 264/289.6; 264/291
[58] Field of Search .............. 428/492, 493, 31, 465; 106/1.23; 264/296, 320, 288.4, 289.6, 291; 156/242

[56] References Cited

U.S. PATENT DOCUMENTS

| | | | |
|---|---|---|---|
| 1,580,857 | 4/1926 | Richards | 428/492 |
| 1,801,666 | 4/1931 | Geer | 428/492 |
| 2,278,722 | 4/1942 | Loiseleur | 457/250 |
| 4,397,706 | 8/1983 | Allen et al. | 156/242 |
| 4,407,871 | 10/1983 | Eisfeller | 428/31 |
| 4,576,156 | 3/1986 | Dyck et al. | 264/320 |
| 4,588,646 | 5/1986 | Athey, Jr. | 428/492 |
| 4,654,271 | 3/1987 | Mauer et al. | 428/465 |
| 4,684,490 | 8/1987 | Taller et al. | 264/296 |
| 4,737,188 | 4/1988 | Bahls | 106/1.23 |
| 4,913,950 | 4/1990 | Riesinger | 428/492 X |

Primary Examiner—Thomas J. Herbert, Jr.
Attorney, Agent, or Firm—Birch, Stewart, Kolasch & Birch

[57] ABSTRACT

A thin, multilayered rubber article and method of making it, having greater resistance to the leakage of fluids therethrough, despite repeated stretching and relaxing of the article within a wide range of movement. The article exhibits a "self-healing" property to impede fluid leakage despite preexisting, or later formed, pinholes or other small openings through the layers. In the method, the base layer is initially stretched before applying an intimately adhered, thinner overlayer of elastomeric material, thereby to provide a stressed interface between the two adhered layers. Additional overlayers can be applied.

17 Claims, 1 Drawing Sheet

SELF-HEALING RUBBER ARTICLE AND METHOD

STATEMENT OF INVENTION

This invention generally relates to improvements in thin sheet rubber articles, and in methods of making them; and more particularly to such improvements that render the articles more imperforate and less subject to leakage of fluids during use despite elastic stretching and relaxing.

BACKGROUND AND PRIOR ART

In the past, thin layers, sheets, and films of natural latex rubber have been widely used for a variety of different products, ranging from decorative articles, protective devices, and many different kinds of medical devices. Such thin rubber articles are often made in seamless form by dipping or otherwise coating a shaped mold into a liquid latex solution and curing the resulting shaped rubber article.

A large proportion of such manufactured articles are often defective and unusable for their intended purposes, due to the formation of small openings, eg pin holes, in the rubber film, as well as thin spots, or weakened areas in the thin rubber layer. Such small openings become enlarged during elastic stretching of the article, and sometimes burst; as does the thin film in the thin spots or weakened areas as the rubber article is stretched.

As a result, such manufacturing imperfections result in undesirably large rejection rates of the resulting products, that in some instances exceed more than 10% of the yield. Particularly in the medical product uses, such imperfections render the articles unsuitable, permitting contaminated body fluids to leak through the small openings in the rubber layer and resulting in the possibility of transmitting infection to persons in contact with the rubber articles.

SUMMARY OF INVENTION

Briefly according to the present invention, there is applied to the thin rubber base layer, or shaped article formed thereof, a thinner overlayer of rubber. The rubber overlayer is intimately adhered to the base layer in such manner as to close and seal pores or pinholes that may have been formed in the base layer. The overlayer is also applied and adhered to the base layer while the base layer is maintained in an elastically stretched condition. As a result, there is provided a differential stressing of the two layers at the interface therebetween, that provides a "self-healing" of the multilayer article to close any small opening or pin holes that may be formed, or developed, in the article during use.

DETAILED DESCRIPTION OF PREFERRED EMBODIMENTS

Figure 1:
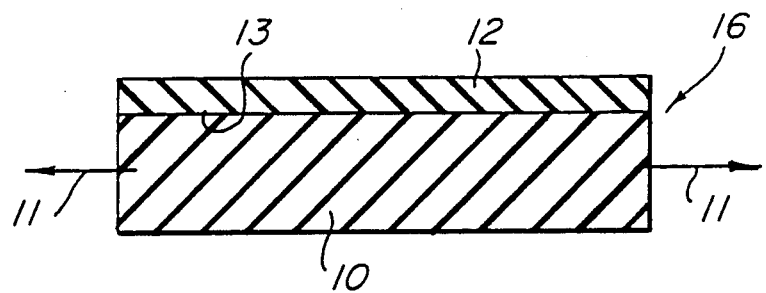
FIG. 1 is a cross sectional view, depicting a portion of a thin rubber article that is stretch coated according to the present invention.

According to one preferred embodiment of the invention, as shown in FIG. 1, a thin base layer of natural latex rubber is linearly stretched, as indicated by the arrowed lines 11, and while maintained in this stretched condition, is uniformly coated with a thinner overlayer 12 of the same rubber material, or of silicone rubber, in such manner as to form an integral bonding of the two layers 10 and 12 at an interface area 13. The thinner overlayer 12 seals pinholes or other small openings in the base layer 10 when stretched, and thereby considerably improves the ability of the resulting laminate to resist the passage of fluids therethrough. The resulting multilayer rubber sheet, or shaped article, is also strenthened, as well as being made more imperforate than the single base layer 10 alone.

Figure 2:
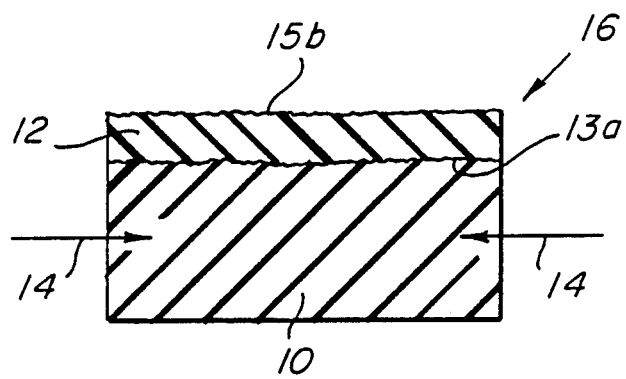
FIG. 2 is a cross sectional view, similar to FIG. 1, and showing the coated article of FIG. 1 in a relaxed state.

When the resulting article is permitted to elastically contract to a more relaxed state, as shown in FIG. 2, the thinner overlayer is compressively stressed, providing an observable fine wrinkling 15b at the outer surface of the overlayer 12, as shown. The contraction of the article is depicted in FIG. 2 by the arrowed lines 14. At the interface region 13a, between the two layers 10 and 12, there is also provided a differentially stressed region, with the interacting portions of the overlayer 12 being maintained in compression whereas those of the base layer 10 being oppositely being in tension.

Thereafter as the dual layer elastomeric article is progressively stretched outward to an extent less than when it was coated (as shown in FIG. 1), the wrinkling 15b at the outside surface of the outerlayer 12 is progressively diminished until returning to the condition shown in FIG. 1. This stretch coated elastomeric product has been found to exhibit two improved properties. Initially, as discussed above, it has been found to be somewhat stronger and more resistant to the passage of fluids therethrough. The second improved property that has been found to exist in the stretch coated article is that of "self-healing" of the article against leakage, in the event that a small pinhole or opening is later formed in the article 16 after it has been stretch coated as described above. In fact, it has been found that the stretch-coating process of FIG. 1 also seals previously formed pinholes, or other very small opening in the base layer 10; and maintains this sealed condition despite repeated stretching and relaxing of the coated article 16, within a limit less than when the overlayer 12 was applied.

More specifically, it has been found that in the event that a small pinhole previously existed, or was later formed, in the stretch-coated article of FIG. 1, that the overlayer 12 seals such opening, and maintains this sealed condition despite repeated stretching and relaxing of the article 16 to an extent less than when it was coated. This self-healing function is believed to result from the compressive stress created in the overlayer 12, and in the interface area 13a between the two layers 10 and 12, as a result of the stretch-coating process. Tests have shown that this self-healing property has been found not to exist in ordinary laminated layers of rubber, when the base layer has not been stretched prior to coating with the overlayer. Such tests have demonstrated that in ordinary multiple layered rubber sheeting, a pinhole previously, or later formed in the article, has been found to leak when the thin rubber article is stretched, and that the leak persists with repeated stretching.

According to one preferred embodiment of the invention, the thin rubber base layer 10 of natural latex rubber is formed by any of the well known processes practised in the prior art, in a variety of different shapes and sizes, by dipping a shaped mold into a liquid latex solution, or otherwise coating the mold. The thickness of the resulting rubber layer is controlled by repeated dipping of the mold, to yield thicknesses in the range of about 0.005 to 0.0012 inches, that have been found most useful for many different products. The base layer can, of course, be formed in other thicknesses.

After curing, the base layer 10 is then stretched to a desired extent using an expandable mold (not shown), or applying the cured layer onto a larger mold to stretch the layer or shaped article to a desired extent. It has been found that the stretch coating process can be satisfactorily performed by stretching the base layer 10 or shaped article, over a range of from 10% greater to 100% greater, or even more, than in its unstretched, relaxed state.

The overlayer 12 is preferably of the same natural latex material, or of silicone rubber, and is applied and intimately adhered to the cured base layer 10, or shaped article thereof, by a similar one of the well known rubber forming processes, including dipping, spraying, or otherwise coating over the cured base 10. The overlayer 12 is preferable formed in thickness ranging from 10% of the thickness of the base layer 10 up to about ⅓ of the thickness of the base layer 10. A thin overlayer 12 is usually desired in order to maintain the thickness of the coated article close to that of the single base layer 10, and to approximate the degree of stiffness or elasticity close to that of the base layer 10 alone. It has been found that the elasticity of the resulting two layer rubber article made according to the present invention remains in the same range as that of the base layer alone. This is believed to result from the fact that the compressive stress resulting in the overlayer 12 when relaxed) are in opposition to the tension stresses created in the base layer 10 by the process. Therefore an externally applied force in a direction to stretch the resulting article 16, is aided by the stresses in the overlayer 12.

Briefly recapitulating the steps of one preferred process according to the invention, a thin base layer 10 of natural latex rubber, or a shaped article formed thereof, is stretched over a range of 10% to 100% greater than the layer in its relaxed state. While maintained in this stretched state, a thin overlayer 12 of the same material, or of silicone rubber, is coated and intimately adhered to the base layer 10, in a thickness ranging from 10% to ⅓ of that of the base layer 10. The coating is cured and the article 16 subsequently removed from its mold and permitted to return to a relaxed state. The resulting article approximates the thickness and degree of elasticity of the single rubber layer alone, yet possesses the improved properties of greater strength and considerably improved resistance to leakage of fluids. Still further, the resulting article possesses a self-healing property that provides sealing of the article against leakage through preexisting pinholes, or those later formed, despite repeated stretching and relaxing of the article, or shaped product formed thereof.

EXAMPLES

A number of thin, latex rubber strips were obtained from standard, commercially available medical grade rubber products, and each was electrically tested for leakage in an electrolyte (saline solution) by detecting the passage of ions therethrough.

All of the strips were then stretched and the electrical tests for leakage were repeated. The tested rubber strips were then divided in three groups:
A. Strips that did not leak (no pinholes or small openings) either before or after stretching.
B. Strips that did not show leakage of ions when tested in their relaxed state but showed leakage when stretched and then tested.
C. Strips that leaked both during tests when relaxed and tests when stretched.

A fourth category was then created:
D. Some of the strips from the first group that did not leak when stretched or relaxed, were then pierced with the point of a small sewing needle.

Each above group A, B, C, and D, were then divided into first and second subgroups. The strips in all of the first subgroups were coated with rubber while in an unstretched state; and those in all of the second subgroups were first stretched and then similarly coated as in the first subgroup but while in their stretched state.

All coated strips were then electrically tested for leakage in an electrolyte, as described above, with the following results:

All strips in the first subgroup of Groups B,C, and D (those that were coated without being first stretched), were found to leak ions whenever the strips were even slightly stretched in the electrolyte. The leakage continued after such strips were then permitted to relax.

In contrast, all strips in the second subgroups of Groups B, C, and D (those that were stretch coated, as above described) did not leak when electrically tested despite repeated stretching and relaxing in the electrolyte. The degree of stretching was limited to that during coating of the base layers.

SECOND SET OF EXAMPLES

A similar series of thin rubber strips was obtained and each was stretched to a different extent (eg 15%, 20%, 25%, 35%, and 50%), and while so stretched was coated with a thinner overlayer of rubber as described above, and then cured.

The strips were electrically tested for leakage as above described; and all exhibited the self-healing property as described above when repeatedly stretched and relaxed during the leak testing. However, each strip was stretched only to the limit corresponding to that when it was coated.

THIRD SET OF EXAMPLES

A similar series of thin rubber strips was obtained and each was stretch coated while being stretched to the same extent as the others. However, each different strip was coated from a different dilution of silicone rubber in a solvent (eg by volume, 10%, 15%, 20%, 25%, 35%, and 50%), using Dow Corning #734 RTV sealant in Dow Corning Cyclomethicone.

The strips were electrically tested as described above, and all exhibited the self-healing property despite repeated stretching and relaxing of the strips during electrical testing (but within the limit of stretching corresponding to that when the strips were coated).

PROGRESSIVE SELF-HEALING

Figure 3:
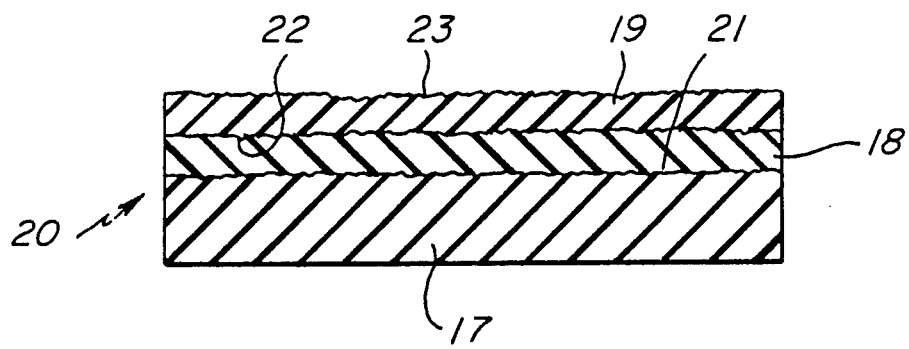
FIG. 3 is a cross sectional view, similar to FIG. 2, and depicting more than one overlayers of rubber, according to a different embodiment of the invention.

In alternative processes as depicted in FIG. 3, a plurality of overlayers of rubber 18, and 19 are applied and integrally adhered to the stretched base layer 17, of rubber, to provide a three layer rubber article, or shaped product thereof. The overlayers 18 and 19 may be successively applied, and successively cured, each on top of the other, as shown, or may be applied on opposite sides of the base layer 17 ( not shown).

The base layer 17 may be differently stretched during the coating of each different one of the overlayers 18 and 19 to impart a progressive self-healing property to the article. Thus, for example, the base layer may be stretched by 45% and the first overlayer 18 applied and cured. Thereafter the article may be stretched by 80% and the second overlayer 19 then applied over the first overlayer 18, and then cured or may be applied on the opposite side of base layer 17). Still additional thin overlayers may be applied on the same or opposite sides, or both, to still further modify the self-healing properties of the resulting article.

It will be appreciated by those skilled in the art that many changes may be made in the described processes, and in the articles, without departing from the spirit and scope of the invention. For example, various different kinds of rubber and related materials may be employed in practising the invention including natural latex rubbers, synthetic rubbers, silicone rubbers, polyurethanes, and other medical grade elastomeric copolymers. The thicknesses of the base layer, and the one or more overlayers, may also be varied to that desired for the applications intended, consistant with providing the necessary strength, elasticity, and/or stiffness of the resulting articles. Since these and other changes can be made, this invention is to be considered as being limited only by the following claims:

What is claimed is:

1. A self-healing multilayer flexible member of rubber comprising:
   a base layer of a rubber, and
   an overlayer of a rubber which is adhered to the base layer of rubber;
   wherein said overlayer of rubber is applied to the base layer as a liquid, while said base layer is maintained in a stretched condition, and thereafter the overlayer is cured while the base layer is maintained in its stretched condition, and wherein small openings in the base layer are sealed.

2. The self-healing member of claim 1, wherein said base layer and said overlayer comprise silicone rubber or latex rubber.

3. A progressive self-healing multilayer flexible member of rubber comprising:
   a base layer of a rubber,
   a first overlayer of a rubber which is adhered to the base layer of a rubber, and
   a second overlayer of a rubber which is adhered to an outer surface of the base layer or the first overlayer of rubber;
   wherein the first overlayer of rubber is adhered to the base-layer as a liquid while said base layer is maintained in a stretched condition, and thereafter the first overlayer is cured while the base layer is maintained in its stretched condition;
   wherein said second overlayer of rubber is adhered to an outer surface of the base layer, or the first rubber overlayer after it is cured, while said base layer is restretched to a different extent than said previous mentioned stretching; and
   wherein small openings in the base layer are sealed, or small openings in the base layer of rubber and first overlayer of rubber are sealed.

4. A self-healing thin flexible sheet of rubber comprising:
   a thin rubber base layer and a first thin rubber overcoat layer, wherein the first overcoat layer is adhered to the base layer as a liquid, while the base layer is maintained in a stretched condition, and thereafter said first overcoat layer is cured while said base layer is maintained in its stretched condition,
   whereby small openings in the rubber base layer are sealed and there is obtained the self-healing sheet of rubber recited.

5. The flexible sheet of claim 4, wherein said base layer and said first rubber overcoat layer comprise latex rubber or silicone rubber.

6. The flexible sheet of claim 4, further comprising a second thin liquid coating of rubber which is adhered to said base layer, or adhered to the first rubber overcoat layer after the first overcoat layer's curing, while the base layer is restretched to a different extent than said first mentioned stretching; and thereafter the second coating of rubber is cured while the base layer is maintained in said restretched condition;
   whereby small openings are sealed in the layer to which said second overcoat layer is adhered.

7. The flexible sheet of claim 6, wherein said base layer, first rubber overcoat layer and second rubber overcoat layer comprise latex rubber or silicone rubber.

8. A self-healing thin flexible multilayered article of latex rubber comprising:
   a thin flexible base layer of latex rubber,
   a thinner, flexible overlayer of latex rubber intimately adhered to the surface of the base layer when the base layer is maintained in a stretched condition,
   said thin, flexible, overlayer, sealing small openings in the base layer when the base layer is stretched,
   whereby flexing and stretching of the resulting multilayered article to an extent less than said given stretched condition provides self-healing of later formed small openings in the base layer and overlayer.

9. A method for making a self-healing multilayer flexible rubber member having a stressed interface between two layers thereof, comprising the steps of:
   (a) stretching a first flexible rubber base member to a stretched condition;
   (b) coating the flexible rubber base member with a thin liquid coating layer of a rubber while maintaining the flexible rubber member in its stretched condition, and
   (c) curing the thin coating of rubber while maintaining the flexible rubber member in its stretched condition,
   whereby small openings in the base layer are sealed and there is obtained the self-healing multilayer member recited.

10. The method of claim 9, wherein said rubber coating layer comprises silicone rubber.

11. The method of claim 9, wherein said rubber coating layer comprises latex rubber.

12. A method for making a progressive self-healing multilayer flexible rubber member having 2 stressed interfaces between layers thereof, comprising the steps of:
    (a) stretching a first flexible rubber base member to a stretched condition,
    (b) coating the flexible rubber member with a first thin liquid coating layer of a rubber while maintaining the flexible latex rubber member in its stretched condition, (c) curing the first thin coating of rubber while maintaining the flexible rubber member in its stretched condition, (d) restretching the rubber base member after curing step (c), to a different extent than the first mentioned stretching, (e) applying a second thin liquid coating of a rubber to an outer surface of said first thin rubber coating or said base member, while maintaining said rubber base member in said restretched condition, and (f) curing said second rubber coating layer while maintaining the rubber base member in said last mentioned restretched condition, whereby small openings in the base layer are sealed, or small openings in the base layer and the first thin rubber coating are sealed, and there is obtained the progressive self-healing multilayer member recited.

13. The method of claim 12, wherein said first and second thin liquid coating layers comprise latex rubber or silicone rubber.

14. A method for making a self-healing flexible member of rubber, comprising the steps of:

(a) stretching a base layer of a rubber to a stretched condition of 10% or more, (b) adhering a thin liquid layer of a rubber to said base layer while maintaining said base layer in said stretched condition, and (c) curing the thin coating of rubber while maintaining the flexible rubber member in its stretched condition, whereby small openings in the base layer are sealed and there is obtained the self-healing member recited.

15. A method of making a self-healing flexible multilayer member of rubber comprising the steps of:

(a) stretching a rubber base layer in two dimensions to a stretched condition of 10% to 100%, (b) applying a liquid thin overlayer of a rubber to said base layer, while maintaining the base layer in said stretched condition, and (c) curing said overlayer of rubber while maintaining said base layer in its stretched condition, whereby small openings in the base layer are sealed and there is obtained the self-healing member of rubber recited.

16. A method of making a progressive self-healing flexible member of rubber, comprising the steps of:

(a) stretching a base layer of a rubber to a stretched condition of 10% or more, (b) adhering a first thin liquid layer of a rubber to said base layer while maintaining said base layer in said stretched condition, (c) curing the first thin coating of rubber while maintaining the flexible rubber member in its stretched condition, (d) restretching the base layer to a different degree of stretching than said first mentioned stretching, (e) adhering a second thin layer of a rubber to said base layer or to the first adhered layer, while maintaining the base layer in said restretched condition, and (f) curing said second rubber coating while maintaining the flexible rubber member in said restretched condition, whereby small openings in the base layer are sealed, or small openings in the base layer and first overlayer are sealed, and there is obtained the progressive self-healing member recited.

17. The method of claim 16, wherein said base layer, said first adhered layer, and said second adhered layer comprise latex rubber or silicone rubber.

* * * * *